(12) United States Patent
Colvin et al.

(10) Patent No.: US 10,030,124 B2
(45) Date of Patent: Jul. 24, 2018

(54) MODIFIED FILLERS FOR RUBBER COMPOUNDING AND MASTERBATCHES DERIVED THEREFROM

(71) Applicants: Cooper Tire & Rubber Company, Findlay, OH (US); Industrias Negromex, S.A. De C.V., Altamira (MX)

(72) Inventors: Howard Colvin, Wayne, OH (US); Peter John Wallen, Findlay, OH (US)

(73) Assignee: Cooper Tire & Rubber Company, Findlay, OH (US)

( * ) Notice: Subject to any disclaimer, the term of this patent is extended or adjusted under 35 U.S.C. 154(b) by 27 days.

(21) Appl. No.: 14/753,376

(22) Filed: Jun. 29, 2015

(65) Prior Publication Data
US 2015/0376380 A1     Dec. 31, 2015

Related U.S. Application Data

(60) Provisional application No. 62/018,886, filed on Jun. 30, 2014.

(51) Int. Cl.
| | |
|---|---|
| *C08K 9/06* | (2006.01) |
| *C07F 7/18* | (2006.01) |
| *B60C 1/00* | (2006.01) |
| *C09C 1/30* | (2006.01) |
| *C08K 3/36* | (2006.01) |

(52) U.S. Cl.
CPC ............ *C08K 9/06* (2013.01); *B60C 1/00* (2013.01); *C07F 7/1836* (2013.01); *C07F 7/1892* (2013.01); *C09C 1/3081* (2013.01); *C08K 3/36* (2013.01)

(58) Field of Classification Search
CPC ..... C07F 7/1836; C07F 7/1892; C09C 1/3081

USPC ........................................................ 106/490
See application file for complete search history.

(56) References Cited

U.S. PATENT DOCUMENTS

| | | |
|---|---|---|
| 5,445,756 A | 8/1995 | Didier et al. |
| 5,445,759 A | 8/1995 | Powell |
| 6,420,456 B1 | 7/2002 | Koski |
| 6,713,534 B2 | 3/2004 | Goerl et al. |
| 7,074,457 B2 | 7/2006 | Panz et al. |
| 7,312,271 B2 | 12/2007 | Chen et al. |
| 8,357,733 B2 | 1/2013 | Wallen et al. |
| 2006/0106143 A1 | 5/2006 | Lin et al. |
| 2010/0108277 A1 | 5/2010 | Meisel et al. |
| 2010/0181525 A1 | 7/2010 | Belmont |
| 2014/0083598 A9 | 3/2014 | Wallen et al. |

OTHER PUBLICATIONS

JP 2011/102451 machine translation (2016).*

* cited by examiner

*Primary Examiner* — Edward J Cain
(74) *Attorney, Agent, or Firm* — Jacob M. Ward; Ward Law Office LLC

(57) ABSTRACT

A method for manufacturing a modified silica product includes admixing a mercapto silane and a silica to form a hydrophobated silica, and treating the hydrophobated silica with an oxidizing agent. Likewise, a method for manufacturing a silica masterbatch with the modified silica product includes the admixing a mercapto silane solution and a silica slurry to form a hydrophobated silica slurry, and then treating the hydrophobated silica slurry with an oxidizing agent to form a modified silica slurry. The modified silica slurry is blended with a rubber latex, which is then coagulated to form the silica masterbatch. Rubber formulations and articles manufactured with one of the modified silica product and the silica masterbatch are also disclosed.

12 Claims, 3 Drawing Sheets

MODIFIED FILLERS FOR RUBBER COMPOUNDING AND MASTERBATCHES DERIVED THEREFROM

CROSS-REFERENCE TO RELATED APPLICATIONS

This application claims the benefit of U.S. Provisional Application No. 62/018,886, filed on Jun. 30, 2014. The entire disclosure of the above application is hereby incorporated herein by reference.

FIELD

The present disclosure relates to reinforcing fillers for rubber compounds and, more particularly, to a modified silica filler for rubber compounds.

BACKGROUND

In making tires and other rubber products, it is desirable to mix silica with an elastomer or rubber to improve certain properties of the elastomer. It is well known to incorporate silica into rubber using a dry mixing process, where a material is put on the surface of the silica during the mixing process to allow it to blend into the rubber. When the silica is coated with such an agent, the silica is referred to as hydrophobated, and any material used to make hydrophobated silica is a hydrophobating agent.

A variety of silane compounds have been developed as hydrophobation agents. Known silane compounds and processes for incorporating silica into rubber are described in U.S. Pat. No. 8,357,733 to Wallen et al.

One known class of silane is mercapto silane, which has an active thiol group and offers excellent coupling between rubber and silica. A commercially available mercapto silane, which has desirable water solubility when hydrolyzed, is 3-mercaptopropyl trimethoxy silane, having the following structure.

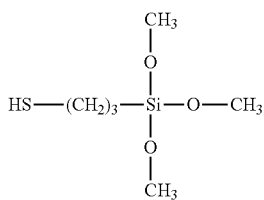

A disadvantage of using mercapto silane as a hydrophobating agent is that it tends to contribute to poor scorch resistance or scorch time, in both conventional rubber compounds and when used in the silica masterbatch process. Scorch is a reflection of the fully compounded rubber's ability to be thermally processed without premature vulcanization or crosslinking, and it is a very important parameter in processing rubber. As the rubber begins to crosslink, it can no longer be extruded and/or formed into a useful article. Thus, longer scorch times are desirable. Rubber compounds with longer scorch times can be processed at higher temperature, and can be reworked more than rubber with shorter scorch times. Compounds with longer scorch times can significantly improve tire plant productivity.

Blocked mercapto silanes are also known, in which the thiol group undergoes a preliminary reaction with another chemical constituent to become essentially unreactive under normal mixing conditions, but when heated to a higher temperature will react as though the thiol group were present in its original condition. The processing behavior of blocked mercapto silanes is very good. However, the use of known types of blocked mercapto silane is cost prohibitive in many rubber applications.

There is a continuing need for a method by which mercapto silane may be used as a hydrophobating agent in rubber compounds and a silica masterbatch process. Desirably, the method permits the use of commercially available mercapto silane while providing sufficient scorch resistance.

SUMMARY

In concordance with the instant disclosure, a method by which mercapto silane may be used as a hydrophobating agent in rubber compounds and a silica masterbatch process, and which permits the use of commercially available mercapto silane while providing sufficient scorch resistance, is surprisingly discovered.

The present disclosure includes a process by which silica hydrophobated with mercapto silane, for example, 3-mercaptopropyl trimethoxysilane or 3-mercaptopropyl methyldimethoxysilane, is treated with an oxidizing agent to form a modified silica product. The oxidizing agent is chosen to oxidize the mercaptan or thiol group of the silica bound mercapto silane. The oxidizing is generally performed under alkaline or substantially neutral pH conditions. More specifically, treatment of hydrophobated silica with oxidizing agents such as hydrogen peroxide or sodium hypochlorite provides a modified silica product which, when incorporated into a rubber compound or silica masterbatch, has excellent compounded properties with improved scorch time.

In one embodiment, a method for manufacturing a modified silica product includes the step of admixing a mercapto silane and a silica to form a hydrophobated silica. The hydrophobated silica is then treated with an oxidizing agent to form the modified silica product.

Rubber formulations and articles such as tires made with the modified silica product are also within the scope of the present disclosure.

In another embodiment, a method for manufacturing a modified silica product includes the step of admixing a mercapto silane solution and a silica slurry to form a hydrophobated silica slurry. The hydrophobated silica slurry is then treated with an oxidizing agent to form a modified silica slurry. The modified silica slurry is blended with a rubber latex, which is subsequently coagulated to form a silica masterbatch having the modified silica product.

Rubber formulations and articles such as tires made with the silica masterbatch with the modified silica product are further within the scope of the present disclosure.

DRAWINGS

The above, as well as other advantages of the present disclosure, will become readily apparent to those skilled in the art from the following detailed description, particularly when considered in the light of the drawings and tables described hereafter.

DETAILED DESCRIPTION

Figure 1:
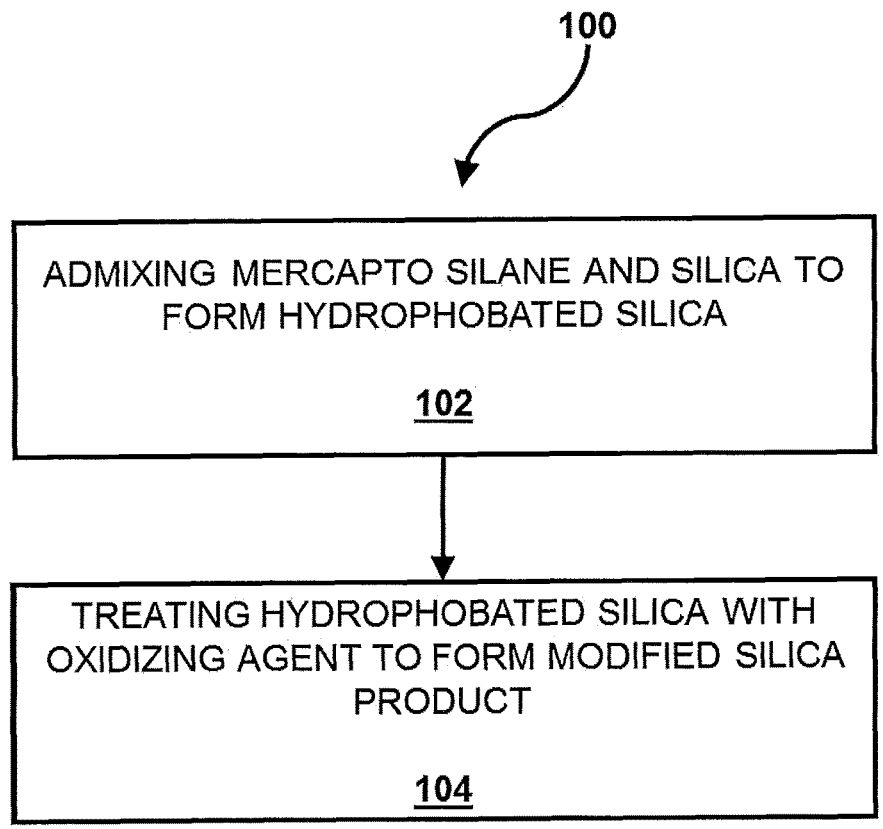
FIG. 1 is a flow diagram illustrating a method of forming a modified silica product according to one embodiment of the disclosure.

The following description is merely exemplary in nature and is not intended to limit the present disclosure, application, or uses. It should also be understood that throughout the drawings, corresponding reference numerals indicate like or corresponding parts and features. In respect of the methods disclosed, the order of the steps presented is exemplary in nature, and thus, is not necessary or critical unless otherwise disclosed.

As shown in FIG. 1, the present disclosure includes a method 100 for manufacturing a modified silica product. The method 100 involves a step 102 of admixing mercapto silane and silica to form a hydrophobated silica. The method 100 also includes a step 104 of treating the silica that has been hydrophobated with a mercapto silane with an oxidizing agent. The modified silica product is particularly useful in compounding all types of elastomers for any application that involves a sulfur cure or vulcanization.

Figure 2:
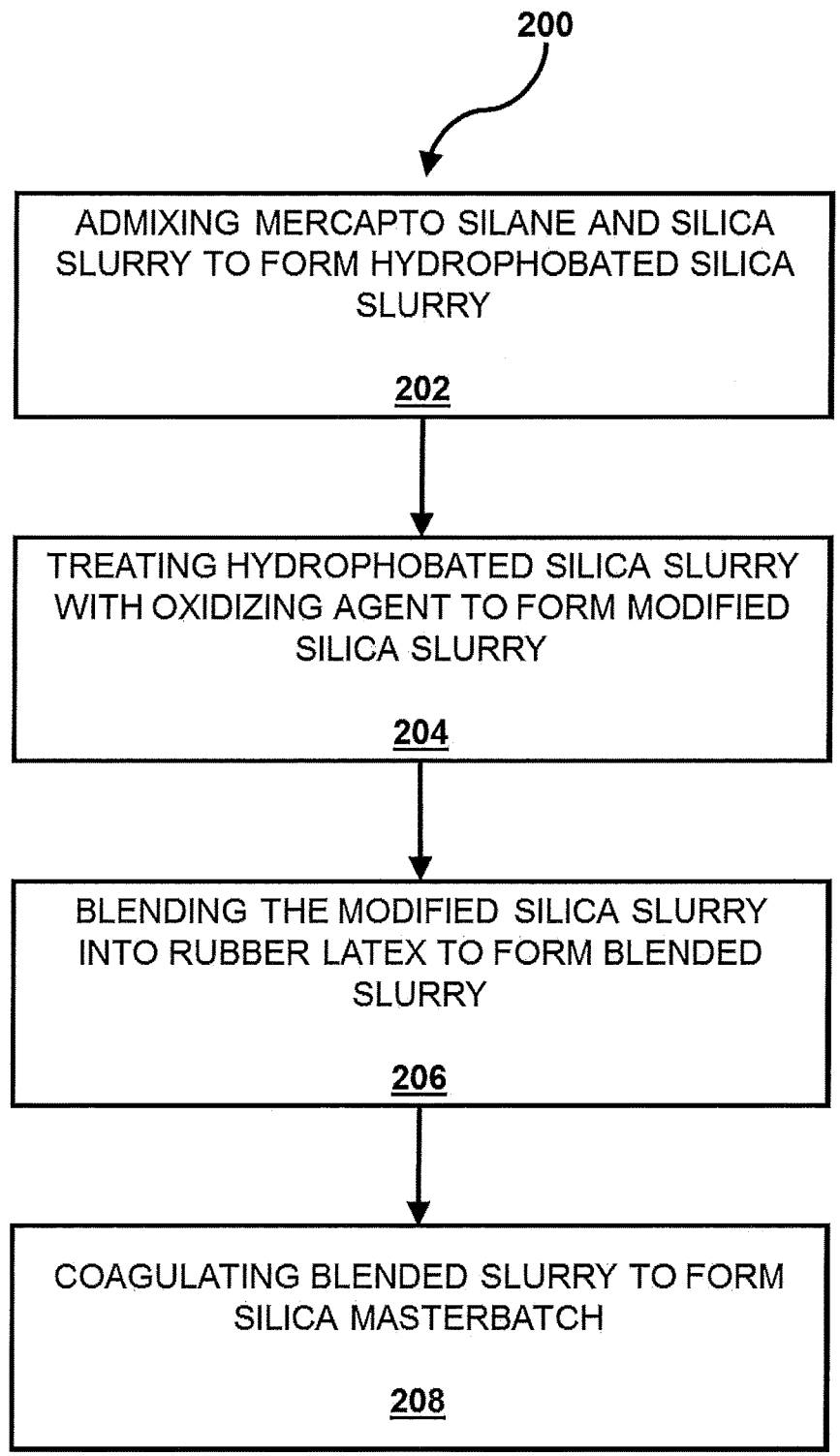
FIG. 2 is a flow diagram illustrating a method of forming a modified silica masterbatch according to one embodiment of the disclosure.

Referring to FIG. 2, the present disclosure also includes a method 200 for manufacturing the modified silica product in a silica masterbatch. The method 200 involves a step 202 of admixing mercapto silane and silica slurry to form hydrophobated silica slurry. The hydrophobated silica slurry is then treated with the oxidizing agent to form a modified silica slurry in a step 204. In a step 206, the modified silica slurry is blended into a rubber latex to form a blended slurry. The blended slurry is subsequently coagulated in a step 208 to form the modified silica product in the silica masterbatch.

Where the modified silica product formed by the methods of FIG. 1 or 2 has been compounded in polymer or silica masterbatch, the resulting compound exhibits improved scorch time over corresponding silica that has not been so treated. Any suitable polymer may be used with the modified silica product of the present disclosure, including, but not limited to: natural rubber (NR); polymers made from one or more conjugated dienes having from 4 to 12 carbon atoms, preferably from 4 to 6 carbon atoms such as butadiene or isoprene; polymers made from a conjugated diene having from 4 to 12 carbon atoms with a vinyl substituted aromatic having from 7 to 12 carbon atoms such as styrene, alpha-methyl styrene, vinylpyridine, and the like; polymers and copolymers made from chloroprene (that is polychloroprene); various halogen-containing polymers such as copolymers of vinylidene fluoride and hexafluoropropylene; acrylic rubbers including polymers and copolymers of alkyl acrylates; nitrile rubber; and combinations thereof. As particular nonlimiting examples, suitable polymers may include SBR, BR, NR, NBR, chloroprene or blends thereof. It should be appreciated that the hydrophobated silica product may be compounded in other suitable types of polymers, as desired.

Figure 3:
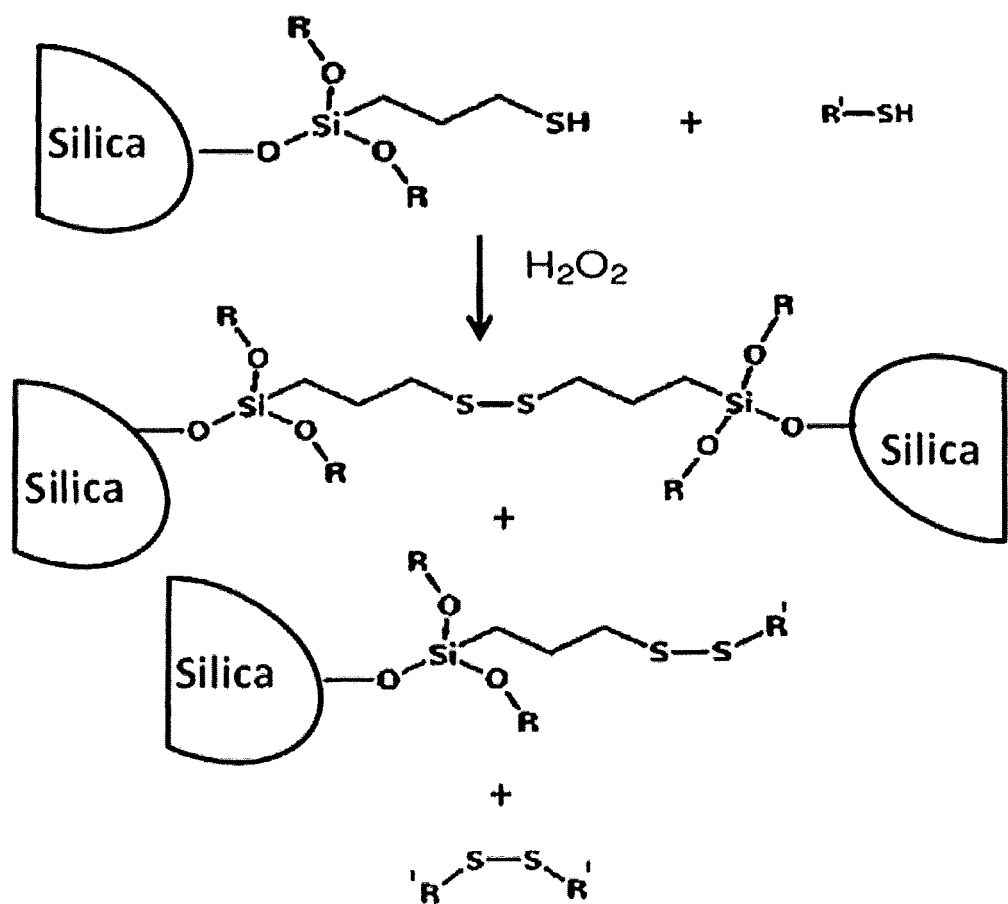
FIG. 3 is a schematic diagram showing an exemplary reaction of hydrophobated silica with mercapto silane and an oxidizing agent.

Any oxidizing agent suitable to convert a mercaptan group to a disulphide under suitable conditions, for example, as depicted in FIG. 3, may be used within the scope of the disclosure. As particular nonlimiting examples, the oxidizing agent may include at least one of hydrogen peroxide, organic hydroperoxide, hypochlorite (bleach), perborate, permanganate, copper (II) sulphate, bromine, nitric oxide (NO) and combinations thereof. The oxidizing agent is employed in a concentration sufficient to oxidize at least a major portion of the mercaptan groups of the mercapto silane. For example, an excess of oxidizing agent may be employed to convert substantially all of the mercaptan groups to disulphide. One of ordinary skill in the art may select other suitable types and concentrations of the oxidizing agent, as desired.

It should be understood that the oxidizing of the mercaptan group may be performed at substantially neutral to basic pH, in the case of hydrogen peroxide or hypochlorite. While not wishing to limit the process to any particular chemistry, the oxidation of mercaptan groups is believed to advantageously take place under alkaline conditions, or can be catalyzed by addition of an alkali metal iodide salt under neutral conditions, to form disulfides. Treatment of mercaptan groups under acidic conditions with hydrogen peroxide is believed to lead to a sulfonic acid. Thus, conditions that provide an acidic pH may undesirably result in the formation of sulfonic acid, as opposed to disulfide, and may not provide sufficient scorch resistance when compounded in rubber formulations.

The present method may be employed with a variety of silica types, having a broad range of surface areas and a broad range of BET/CTAB ratios. A variety of silica types are suitable for use in the modified silica product of the present disclosure, including amorphous silica and fumed silica products. In a most particular embodiment, the silica used in the modified silica product is amorphous silica. Representative examples of commercially available silica which conform to the above requirements include silicas sold by Solvay under the designations Z1165MP (165 m$^2$/g BET specific surface area), and Zeosil® Premium 200MP (220 m$^2$/g BET specific surface area). Additional silicas are commercially available from Evonik Industries under the designations Ultrasil® 7000 GR (190 m$^2$/g BET specific surface area) and Ultrasil® VN3 (190 m$^2$/g BET specific surface area) and from Huber under the designations Zeopol® 8745 (180 m$^2$/g BET specific surface area) and Zeopol® 8755 (190 m$^2$/g BET specific surface area). Other suitable types of silica may also be used within the scope of the disclosure, as desired.

The modified silica product of the disclosure is also suitable for incorporation into all types of silica masterbatch, whether they are based on an emulsion polymer using the process described in U.S. Pat. No. 8,357,733 to Wallen et al., or a solution polymer as described in U.S. Pat. No. 6,420,456 to Koski et al., U.S. Pat. No. 6,713,534 to Goerl et al., and U.S. Pat. No. 7,312,271 to Chen et al.

The present disclosure also includes a rubber formulation having a quantity of elastomer, and a quantity of the modified silica product. The particles of the modified silica product may be substantially evenly distributed throughout the elastomer, for example, by a mixing operation prior to an extrusion or molding operation. It should be understood that the substantially even distribution of the modified silica product throughout the elastomer may be facilitated by a thorough mixing operation, and that the ability to perform such mixing operations is possessed by of one of ordinary skill in the art.

The rubber formulation can be compounded by methods known in the rubber compounding art, such as mixing various sulfur-vulcanizable constituent polymers with various commonly used additive materials as, for example, curing aids such as sulfur, activators, retarders and accelerators, processing additives such as oils, resins, for example, tackifying resins, silicas, plasticizers, fillers, pigments, fatty acids, zinc oxide, waxes, antioxidants and antiozonants, peptizing agents, and reinforcing materials such as, for example, carbon black, and the like. Other suitable additives for rubber formulations may also be used, as desired. Depending on the intended use of the rubber formulation, the common additives are selected and used in conventional amounts.

In another embodiment according to the present disclosure, other additives having mercaptan groups may also be incorporated into the modified silica by first adding the additive having a mercaptan group to the aqueous slurry of the modified silica followed by or concomitant with the oxidizing agent. This is illustrated in FIG. 3 where the additive is represented by R'—SH. It should be appreciated that by incorporation of R'—SH into the mixture, a variety of species may be produced.

A non-limiting example of such an additive is 2-mercapto benzothiazole (MBT) accelerant having the following structure.

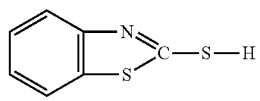

It should be understood that other additives having thiol or mercaptan groups may be selected by a skilled artisan for use in the rubber formulation or silica masterbatch, as desired.

The present disclosure also includes an article comprising the rubber formulation having the modified silica product. It should be appreciated that the rubber formulation having the modified silica product may be extruded, molded, or otherwise formed into a desired shape and cured through the application of at least one of heat and pressure. As a nonlimiting example, the rubber formulation may be used in a tire having a component such as a tire tread, sidewall, belt coat, or another component of the tire. Other types of articles including commercial products may also be manufactured using the rubber formulation with the modified silica product, within the scope of the disclosure.

EXAMPLES

Example A

Preparation of silica hydrophobated with 3-mercaptopropyl trimethoxysilane (Silquest™ A-189, commercially available from Momentive Performance Materials), followed by treatment with hydrogen peroxide.

An aqueous slurry of 6.20% Ultrasil® 7000 silica was prepared. This slurry (786.5 grams, containing 48.76 grams of silica) was added to a two liter beaker and heated to 160° F.

Separately, 3-mercaptopropyl trimethoxysilane (3.17 grams) was dissolved in isopropyl alcohol (4 ml) in a 250 ml beaker. Acetic acid (0.7 ml) was added to the silane solution. Water (50 ml) was slowly added to the silane solution over a period of 15 min period to complete the hydrolysis.

The hydrolyzed silane solution was added to the silica slurry and stirred for 10 minutes. The pH of the resulting slurry was raised to 7.5-7.8 using a dilute sodium hydroxide solution. This slurry was heated at 160° F. for two hours with stirring to complete the hydrophobation reaction.

A 31% hydrogen peroxide solution (0.81 grams) was diluted to 20 ml with water and then added to the hydrophobated silica slurry. This mixture was heated for an additional hour at 160° F.

Blended SBR lattices (SBR 1502 latex and SBR 1712 latex, without oil) of an 18.78% solids content (399.45 grams) was adjusted to a pH of 11 using a solution of sodium hydroxide. The resulting silica slurry was added to the blended SBR latices with stirring in such a manner as to maintain the final latex/silica slurry pH at 9.5-9.8, in order to avoid any coagulation.

A separately prepared mixture of highly aromatic oil (22.5 grams) and ground N-(1,3-dimethylbutyl)-N'-phenyl-P-phenylenediamine or 6PPD (0.30 grams), which had been heated to 212° F., was added to the silica/latex slurry at 160° F. and stirred vigorously for 15 minutes. A solution of anhydrous calcium chloride (8 grams dissolved in 500 ml of water) was slowly added to the silica/latex slurry to obtain the coagulated silica masterbatch.

The resulting silica masterbatch (SMB) was dewatered with a filter cloth and dried in a circulating air oven at 130° F. for 4-5 hours.

Example B

Preparation of silica hydrophobated with 3-mercaptopropyl trimethoxysilane, followed by treatment with sodium hypochlorite.

An aqueous slurry of 6.20% Ultrasil® 7000 silica was prepared. This slurry (786.5 grams, containing 48.76 grams of silica) was added to a two liter beaker and heated to 160° F.

Separately, 3-mercaptopropyl trimethoxysilane (3.17 grams) was dissolved in isopropyl alcohol (4 ml) in a 250 ml beaker. Acetic acid (0.7 ml) was added to the silane solution. Water (50 ml) was slowly added to the silane solution over a period of 15 min period to complete the hydrolysis.

The hydrolyzed silane solution was added to the silica slurry and stirred for 10 minutes. The pH of the resulting slurry was raised to 7.5-7.8 using a sodium hydroxide solution. This slurry was heated at 160° F. for two hours to complete the hydrophobation reaction.

A 4.59% sodium hypochlorite solution (11.80 grams) was diluted to 20 ml with water and then added to the hydrophobated silica slurry. This mixture was heated for an additional hour at 160° F. Blended SBR latices (SBR 1502 latex and SBR 1712 latex, without oil) of an 18.78% solids content (399.45 grams) was adjusted to a pH of 11 using a solution of sodium hydroxide. The resulting silica slurry was added to the blended SBR latices with stirring in such a manner as to maintain the final latex/silica slurry pH at 9.5-9.8, in order to avoid any coagulation.

A separately prepared mixture of highly aromatic oil (22.5 grams) and ground N-(1,3-dimethylbutyl)-N'-phenyl-P-phenylenediamine or 6PPD (0.30 grams), which had been heated to 212° F., was added to the silica/latex slurry at 160° F. and stirred vigorously for 15 minutes. A solution of anhydrous calcium chloride (8 grams dissolved in 500 ml of water) was slowly added to the silica/latex slurry to obtain the coagulated silica masterbatch.

The resulting silica masterbatch (SMB) was dewatered with a filter cloth and dried in a circulating air oven at 130° F. for 4-5 hours.

Example C

Preparation of rubber formulations with modified silica product.

A series of experimental rubber formulations having the modified silica product of the present disclosure, with varying mole ratios of peroxide to 3-mercaptopropyl trimethoxysilane, is shown below in TABLE 1. It should be understood that all formulations are described relative to 100 parts per hundred rubber or elastomer (PHR), on a per weight basis, with elastomer in the silica master batch (SMB) having the modified silica product contributing to the 100 total parts of elastomer in the experimental rubber formulations in which the modified silica product was used.

without an oxidizing treatment according to the present disclosure. The hydrophobated silica in the control rubber formulation may be manufactured substantially as described in U.S. Pat. No. 8,357,733 to Wallen et al., as a nonlimiting example.

TABLE 1

| Description | Molar ratio of Peroxide to Silane | | | | |
|---|---|---|---|---|---|
| | 0% | 10% | 30% | 50% | 100% |
| SMB 61 phr silica 31 phr oil - Control - A-189, no peroxide | 96.00 | — | — | — | — |
| SMB 65 phr silica 31 phr oil - A-189, 0.1 moles peroxide/mole SH | — | 91.00 | — | — | — |
| SMB 65 phr silica 31 phr oil - A-189, 0.3 moles peroxide/mole SH | — | — | 91.00 | — | — |
| SMB 65 phr silica 31 phr oil - A-189, 0.5 moles peroxide/mole SH | — | — | — | 91.00 | — |
| SMB 65 phr silica 31 phr oil - A-189, 1.0 moles peroxide/mole SH | — | — | — | — | 91.00 |
| SBR 1712 | 13.80 | 14.84 | 14.84 | 14.78 | 14.75 |
| SBR 1502 | 21.11 | 23.37 | 23.37 | 23.25 | 23.19 |
| Butadiene, High Cis | 20.00 | 20.00 | 20.00 | 20.00 | 20.00 |
| Carbon Black | 45.00 | 45.00 | 45.00 | 45.00 | 45.00 |
| Process oil | 5.20 | 6.24 | 6.24 | 6.59 | 7.14 |
| Antioxidant/Antiozonant | 2.80 | 2.82 | 2.82 | 2.82 | 2.82 |
| Wax | 1.50 | 1.50 | 1.50 | 1.50 | 1.50 |
| ZnO | 3.00 | 3.00 | 3.00 | 3.00 | 3.00 |
| Stearic acid | 1.00 | 1.00 | 1.00 | 1.00 | 1.00 |
| Accelerator | 2.65 | 2.65 | 2.65 | 2.65 | 2.65 |
| Sulfur | 1.60 | 1.60 | 1.60 | 1.60 | 1.60 |
| Total | 213.66 | 213.02 | 213.02 | 213.18 | 213.64 |

The control rubber formulation was mixed according to a conventional two pass mixing cycle. The experimental rubber formulations were also mixed according to the conventional two pass mixing cycle, to ensure a similar shear history for all of the rubber formulations.

The control and experimental rubber formulations were then characterized according to a battery of conventional rheometric and physical tests, as shown below in TABLE 2 and TABLE 3, respectively.

TABLE 2

| Rheometry - | Molar ratio of Peroxide to Silane | | | | |
|---|---|---|---|---|---|
| 340° F. x 24 m | 0% | 10% | 30% | 50% | 100% |
| Min. Torque, ML | 2.1 | 2.1 | 2.1 | 2.1 | 2.0 |
| Max. Torque, MH | 11.5 | 12.6 | 13.9 | 13.7 | 13.4 |
| T-60 | 0.9 | 1.0 | 1.5 | 1.7 | 1.7 |
| T-95 | 2.5 | 1.6 | 2.0 | 2.5 | 2.5 |
| Ts1 | 0.69 | 0.78 | 1.10 | 1.26 | 1.27 |
| Ts2 | 0.75 | 0.86 | 1.21 | 1.38 | 1.39 |
| Mooney, ML 1 + 4 @ 212° F. | 68 | 67 | 67 | 67 | 66 |
| Scorch, Ts5 @ 275° F. | 5.7 | 6.2 | 9.2 | 11.1 | 11.4 |
| Scorch, Ts10 @ 275° F. | 6.2 | 6.7 | 9.9 | 11.8 | 12.2 |

As illustrated in TABLE 2, the experimental rubber formulations having the modified silica product of the present disclosure exhibit significant improvements in scorch resistance, in comparison to the control rubber formulation having silica hydrophobated with mercapto silane

TABLE 3

| Stress/Strain - | Molar ratio of Peroxide to Silane | | | | |
|---|---|---|---|---|---|
| 340° F. x 15 m Original | 0% | 10% | 30% | 50% | 100% |
| M100 | 304 | 277 | 293 | 251 | 258 |
| M200 | 798 | 704 | 753 | 566 | 573 |
| M300 | 1529 | 1360 | 1443 | 1112 | 1096 |
| Tensile | 2482 | 2909 | 2627 | 2623 | 2678 |
| % Elongation | 432 | 552 | 479 | 557 | 590 |
| Hardness | 67 | 69 | 69 | 70 | 70 |

The physical properties shown in TABLE 3 also reveal a sufficient level of reinforcement in cured products with the modified silica product, in comparison to the control rubber formulation. Performance testing was also performed, including dynamic property testing, abrasion, and dispersion, and the experimental rubber formulations deemed satisfactory in comparison to the control rubber formation.

Testing of experimental rubber formulations relative to control rubber formulations having non-mercapto silane hydrophobating agents, such as bis-(3-trimethoxysilylpropyl)-disulfide (TMSPD) has also been performed. The experimental rubber formulations were observed to have scorch safety similar to the control rubber formulations with TMSPD.

Experimental silica masterbatch formulations having both a mercapto silane and MBT treated with oxidizing agent (peroxide) were also assessed. The experimental silica masterbatch formulations having both the mercapto silane and the MBT were observed to have sufficient scorch safety.

Advantageously, the modified silica product or silica masterbatch of the present disclosure permits the use of commercially available mercapto silanes in rubber formulations, while providing sufficient scorch resistance not heretofore observed with non-blocked mercapto silane hydrophobating agents.

While certain representative embodiments and details have been shown for purposes of illustrating the invention, it will be apparent to those skilled in the art that various changes may be made without departing from the scope of the disclosure, which is further described in the following appended claims.

What is claimed is:

1. A method for manufacturing a modified silica product, the method comprising the steps of:
   admixing a mercapto silane and a silica to form a hydrophobated silica; and
   treating the hydrophobated silica with an oxidizing agent at a temperature permitting a formation of disulfide bonds, wherein the disulfide bonds are formed by oxidation or catalysis of mercaptan groups of the hydrophobated silica to form the modified silica product.

2. The method of claim 1, wherein the oxidizing agent is selected from the group consisting of hydrogen peroxide, organic hydroperoxide, hypochlorite (bleach), perborate, permanganate, copper (II) sulphate, bromine, nitric oxide (NO), and combinations thereof.

3. The method of claim 1, wherein the treating of the hydrophobated silica is performed at one of a substantially neutral pH and a basic pH.

4. The method of claim 1, wherein the mercapto silane is 3-mercaptopropyl trimethoxy silane.

5. A method for manufacturing a modified silica product, the method comprising the steps of:
   admixing a mercapto silane with a non-silane mercaptan containing additive and a silica to form a hydrophobated silica; and
   treating the hydrophobated silica with an oxidizing agent to form the modified silica product.

6. A method for manufacturing a modified silica product, the method comprising the steps of:
   admixing a mercapto silane solution and a silica slurry to form a hydrophobated silica slurry;
   treating the hydrophobated silica slurry with an oxidizing agent at a temperature permitting a formation of disulfide bonds, wherein the disulfide bonds are formed by oxidation or catalysis of mercaptan groups of the hydrophobated silica slurry to form a modified silica slurry;
   blending the modified silica slurry into a rubber latex to form a blended slurry; and
   coagulating the blended slurry to form a silica masterbatch with the modified silica product.

7. The method of claim 6, wherein the oxidizing agent is selected from the group consisting of hydrogen peroxide, organic hydroperoxide, hypochlorite (bleach), perborate, permanganate, copper (II) sulphate, bromine, nitric oxide (NO), and combinations thereof.

8. The method of claim 6, wherein the treating of the hydrophobated silica slurry is performed at one of a substantially neutral pH and a basic pH.

9. The method of claim 6, wherein the mercapto silane solution includes 3-mercaptopropyl trimethoxy silane.

10. The method of claim 6, further comprising the admixing of a non-silane mercaptan containing additive with the mercapto silane solution and the silica slurry.

11. The method of claim 6, wherein the silica masterbatch is solution polymer silica masterbatch.

12. The method of claim 6, further comprising a step of dewatering the silica masterbatch with the modified silica product.

* * * * *